(12) United States Patent
Browning et al.

(10) Patent No.: US 12,039,728 B2
(45) Date of Patent: Jul. 16, 2024

(54) UNCERTAINTY-AWARE DEEP REINFORCEMENT LEARNING FOR ANATOMICAL LANDMARK DETECTION IN MEDICAL IMAGES

(71) Applicant: Covera Health, New York, NY (US)

(72) Inventors: James Browning, Plymouth, MA (US); Li Zhang, Princeton, NJ (US); Benjamin Odry, West New York, NJ (US); Micha Kornreich, New York, NY (US); Jayashri Pawar, Mahwah, NJ (US); Aubrey Chow, Waterford, NY (US); Richard Herzog, New York, NY (US)

(73) Assignee: Covera Health, New York, NY (US)

( * ) Notice: Subject to any disclaimer, the term of this patent is extended or adjusted under 35 U.S.C. 154(b) by 346 days.

(21) Appl. No.: 17/675,765

(22) Filed: Feb. 18, 2022

(65) Prior Publication Data

US 2022/0270248 A1   Aug. 25, 2022

Related U.S. Application Data

(60) Provisional application No. 63/151,433, filed on Feb. 19, 2021.

(51) Int. Cl.
*G06T 7/00* (2017.01)
*G06N 3/04* (2023.01)
*G16H 30/40* (2018.01)

(52) U.S. Cl.
CPC .............. *G06T 7/0012* (2013.01); *G06N 3/04* (2013.01); *G16H 30/40* (2018.01);
(Continued)

(58) Field of Classification Search
CPC .......... G06T 7/0012; G06T 2207/10081; G06T 2207/10088; G06T 2207/20081;
(Continued)

(56) References Cited

U.S. PATENT DOCUMENTS 9,569,736 B1 * 2/2017 Ghesu .................. G06N 20/00
11,604,941 B1 * 3/2023 Hester .................. G06V 10/82
(Continued)

OTHER PUBLICATIONS

Zhang, Jun et al, Detecting Anatomical Landmarks From Limited Medical Imaging Data Using Two-stage Task-Oriented Deep Neural Networks, Oct. 2017, IEEE, IEEE Transactions on Image Processing, pp. 4753-4764 (Year: 2017).*
(Continued)

*Primary Examiner* — Lewis G West
(74) *Attorney, Agent, or Firm* — Polsinelli, P.C.

(57) ABSTRACT

Described are techniques for uncertainty-aware anatomical landmark detection, using, for example, a deep reinforcement learning (DRL) anatomical landmark detection agent. For instance, a process can include generating one or more image features for an input medical image using a first sub-network of the anatomical landmark detection agent. A softmax layer of a second sub-network of the anatomical landmark detection agent can generate a plurality of discrete Q-value distributions for a set of allowable actions associated with movement of the agent within the medical image. An anatomical landmark location within the medical image can be predicted using the discrete Q-value distributions. An uncertainty can be determined for the predicted anatomical
(Continued)

landmark location, based on an average full width half maximum (FWHM) calculated for the plurality of discrete Q-value distributions.

20 Claims, 3 Drawing Sheets

(52) U.S. Cl.
CPC ............... *G06T 2207/10081* (2013.01); *G06T 2207/10088* (2013.01); *G06T 2207/20081* (2013.01); *G06T 2207/20084* (2013.01); *G06T 2207/30004* (2013.01)

(58) Field of Classification Search
CPC ........... G06T 2207/20084; G06T 2207/30004; G06N 3/04; G16H 30/40; G06V 10/454; G06V 10/82; G06V 10/85; G06V 10/25; G06V 2201/03
See application file for complete search history.

(56) References Cited

U.S. PATENT DOCUMENTS

| | | | | |
|---|---|---|---|---|
| 2017/0103532 | A1* | 4/2017 | Ghesu | A61B 5/7264 |
| 2017/0116497 | A1* | 4/2017 | Georgescu | G06N 3/006 |
| 2017/0217102 | A1* | 8/2017 | Mansi | G16H 50/50 |
| 2018/0253837 | A1* | 9/2018 | Ghesu | G06T 7/0012 |
| 2019/0209098 | A1* | 7/2019 | Yu | G06T 7/75 |
| 2022/0366247 | A1* | 11/2022 | Hamrick | G06N 3/04 |
| 2023/0031425 | A1* | 2/2023 | Polisetty | B60W 30/06 |
| 2024/0071122 | A1* | 2/2024 | Ahl | G06V 10/82 |
| 2024/0077969 | A1* | 3/2024 | Moscarillo | G06F 21/83 |
| 2024/0081784 | A1* | 3/2024 | Nikou | A61B 8/463 |

OTHER PUBLICATIONS

Ghesu, Florin-Cristian et al, Multi-Scale Deep Reinforcement Learning for Real-time 3D-Landmark Detection in CT Scans, Jan. 2019, IEEE, IEEE Transactions on Pattern Analysis and Machine Intelligence, pp. 176-189 (Year: 2019).*

Written Opinion in related international application No. PCT/US2022/017037 issued on Feb. 8, 2023.

International Search Report and Written Opinion in related international application No. PCT/US2022/017037 issued on May 25, 2022.

"Partial Policy-Based Reinforcement Learning for Anatomical Landmark Localization in 3D Medical Imagines" by Walid Abdullah Al, et al., IEEE Transactions on Medical IMaging, IEEE, USA, vol. 39, No. 4, Oct. 8, 2019.

"Enhanced Detection of Fetal Pose in 3D MRI by Deep Reinforcement Learning with Physical Structure Priors on Anatomy" by Molin Zhang, et al., Computer Vision—ECCV 2020, 16th European Conference, Glasgow UK, Aug. 23-28, 2020.

"Evaluating Reinforcement Learning Agents for Anatomical Landmark Detection" by Amir Alansary, et al., Medical Image Analysis, vol. 53, Apr. 2019.

"Uncertainty Aware Deep Reinforcement Learning for Anatomical Landmark Detection in Medical Images" by James Browning et al., Computer Vision—ECCV 2020, 16th European Conference, Glasgow UK, Aug. 23-28, 2020.

International Preliminary Report on Patentability Opinion in related international application No. PCT/US2022/017037 issued on May 15, 2023.

* cited by examiner

UNCERTAINTY-AWARE DEEP REINFORCEMENT LEARNING FOR ANATOMICAL LANDMARK DETECTION IN MEDICAL IMAGES

CROSS-REFERENCE TO RELATED APPLICATIONS

This application claims the benefit of priority to U.S. Provisional Patent Application No. 63/151,433 filed Feb. 19, 2021 and entitled 'UNCERTAINTY AWARE DEEP REINFORCEMENT LEARNING FOR ANATOMICAL LANDMARK DETECTION IN MEDICAL IMAGES," the disclosure of which is herein incorporated by reference in its entirety.

TECHNICAL FIELD

The present disclosure pertains to automated pathology detection in medical imaging, and more specifically pertains to improved accuracy and self-assessment in machine learning for anatomical landmark detection.

BACKGROUND

Deep learning (DL) is one example of a machine learning (ML) technique and can be considered a subset of ML. Many deep learning approaches utilize neural networks or neural network architectures. Neural networks can include, but are not limited to, convolutional neural networks (CNNs), recurrent neural networks (RNNs), deep neural networks (DNNs), etc. Deep learning approaches are often referred to as "deep" based on their use of multiple layers to progressively extract higher-level features from a given input of raw data. For example, in a deep neural network, the output of a first layer of artificial neurons becomes an input to a second layer of artificial neurons, the output of a second layer of artificial neurons becomes an input to a third layer of artificial neurons, and so on. Layers that are located between the input and output of the overall deep neural network are often referred to as hidden layers. The hidden layers learn (e.g., are trained) to transform an intermediate input from a preceding layer into a slightly more abstract and composite representation that can be provided to a subsequent layer, until a final or desired representation is obtained as the final output of the deep neural network.

Deep reinforcement learning (DRL) approaches combine reinforcement learning (RL) and deep learning. More particularly, DRL approaches can use deep learning (e.g., a deep neural network with multiple interconnected layers) to solve the Markov decision process of a reinforcement learning algorithm. Reinforcement learning is one of the three basic machine learning paradigms (e.g., alongside supervised learning and unsupervised learning). Unlike supervised learning, in some cases reinforcement learning can be performed without the need for labeled training data that relates each given input to a corresponding desired output. For example, in reinforcement learning, a computational agent learns to make decisions or take actions that maximize a cumulative reward (also referred to as a cumulative return) within a given environment and/or subject to a given set of constraints. The cumulative reward or return may often be specified using a value function. In some examples of reinforcement learning, the computational agent is trained or otherwise learns to make decisions according to a Markov decision process (MDP). In other words, the MDP can be used to represent the problem that is to be solved.

Reinforcement learning that uses a transition probability distribution and reward function associated with the MDP is referred to as model-based reinforcement learning, wherein the transition probability distribution and the reward function collectively comprise the model. Reinforcement learning that does not use a transition probability distribution and reward function associated with the MDP is known as model-free reinforcement learning. Accordingly, model-free reinforcement learning can be used to implement a trial-and-error learning approach. One example of model-free reinforcement learning is known as Q-learning, where the "Q" refers to a function that underlies the Q-learning approach, e.g., a function for the expected rewards for an action taken in a given state.

Deep Q networks (DQNs) combine deep learning with model-free reinforcement learning (e.g., Q-learning). A DQN can be used to determine the value of taking each possible action in a given state. These determined values are known as Q-values or action values. In DQN approaches, one or more policies can be applied to the Q-values determined for a given state or timestep in order to select the next action. Under the DQN approach, the Q-values may be determined as a point estimate for the value of taking each possible action. Distributional DQN (also referred to as "dist-DQN") extends the DQN approach to determine an entire distribution of action values for each action. The use of dist-DQN can provide significantly improved performance in many aspects and may additionally enable more nuanced decision making.

SUMMARY

In some examples, systems and techniques are described for estimating the uncertainty of a machine learning anatomical landmark detection agent. According to at least one illustrative example, a method is provided for anatomical landmark detection, the method including: generating, using a first machine learning sub-network of an anatomical landmark detection agent, one or more image features for a medical image; generating, using at least a softmax layer of a second machine learning sub-network of the anatomical landmark detection agent, a plurality of discrete Q-value distributions for a set of allowable actions associated with movement of the anatomical landmark detection agent within the medical image; predicting an anatomical landmark location within the medical image using the plurality of discrete Q-value distributions; and determining an uncertainty for the predicted anatomical landmark location, wherein the uncertainty is determined based on an average full width half maximum (FWHM) calculated for the plurality of discrete Q-value distributions.

In another example, an apparatus for anatomical landmark detection is provided that includes a memory (e.g., configured to store data, such as virtual content data, one or more images, etc.) and one or more processors (e.g., implemented in circuitry) coupled to the memory. The one or more processors are configured to and can: generate, using a first machine learning sub-network of an anatomical landmark detection agent, one or more image features for a medical image; generate, using at least a softmax layer of a second machine learning sub-network of the anatomical landmark detection agent, a plurality of discrete Q-value distributions for a set of allowable actions associated with movement of the anatomical landmark detection agent within the medical image; predict an anatomical landmark location within the medical image using the plurality of discrete Q-value distributions; and determine an uncertainty for the predicted anatomical landmark location, wherein the uncertainty is determined based on an average full width half maximum (FWHM) calculated for the plurality of discrete Q-value distributions.

In another example, a non-transitory computer-readable medium is provided that has stored thereon instructions that, when executed by one or more processors, cause the one or more processors to: generate, using a first machine learning sub-network of an anatomical landmark detection agent, one or more image features for a medical image; generate, using at least a softmax layer of a second machine learning sub-network of the anatomical landmark detection agent, a plurality of discrete Q-value distributions for a set of allowable actions associated with movement of the anatomical landmark detection agent within the medical image; predict an anatomical landmark location within the medical image using the plurality of discrete Q-value distributions; and determine an uncertainty for the predicted anatomical landmark location, wherein the uncertainty is determined based on an average full width half maximum (FWHM) calculated for the plurality of discrete Q-value distributions.

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. The use of a same reference numbers in different drawings indicates similar or identical items or features. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
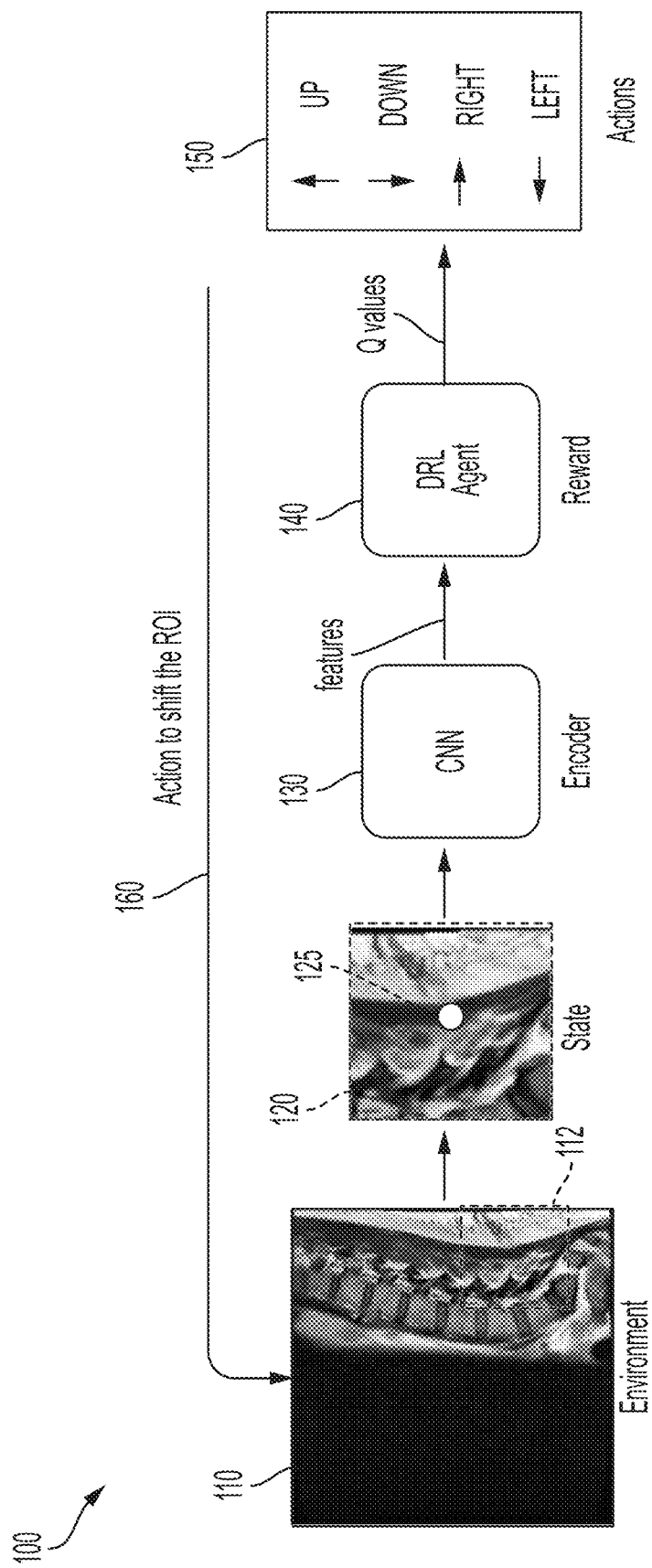
FIG. 1 illustrates an example architecture of a deep reinforcement learning (DRL) network that can be used to detect or locate landmarks in an input image, according to aspects of the present disclosure.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Additional features and advantages of the disclosure will be set forth in the description which follows, and in part will be obvious from the description, or can be learned by practice of the herein disclosed principles. It will be appreciated that for simplicity and clarity of illustration, where appropriate, reference numerals have been repeated among the different figures to indicate corresponding or analogous elements. The description is not to be considered as limiting the scope of the embodiments described herein.

Overview

Disclosed are systems and methods for uncertainty-aware deep reinforcement learning for anatomical landmark detection in medical images. Accurate anatomical landmark detection is an important step in automated pathology detection for medical imaging. Because anatomical landmark detection is often employed as an upstream (e.g., initial) step in a larger process or pipeline for automated medical imaging pathology detection, improvements in the quality and accuracy of the detected anatomical landmarks are desirable. For instance, a pathology detection system may use detected anatomical landmarks to perform field of view (FOV) limiting for an input medical image, in which case the pathology detection system attempts to limit its FOV to only diagnostically relevant anatomical regions. Diagnostically relevant anatomical regions are often located in close proximity to a detected anatomical landmark. Accordingly, the more accurate the detected anatomical landmark is, the finer the FOV limiting that can be applied.

When less accurate anatomical landmark information is provided to the pathology detection system, the use of FOV limiting may become appreciably more likely to introduce errors (e.g., due to over-limiting the FOV). FOV limiting errors can, in some cases, be reduced by restricting the degree or extent to which FOV limiting can be applied, although restrictions on FOV limiting may be seen to reduce the potential benefit otherwise offered by the technique. As such, there is a need for uncertainty aware DRL that can perform accurate anatomical landmark detection in medical images.

Representing uncertainty is an ongoing challenge in the field of deep learning. In some cases, when trained deep learning (and/or DRL, DQN, dist-DQN, etc.) models are utilized in risk-sensitive domains, it can be desirable to achieve reliable quantification of uncertainty in model predictions. For example, when deep learning models are used for medical diagnosis, a reliable quantification of uncertainty in the model predictions can permit the identification of critical mistakes or out-of-distribution data. Subsequently, any critical mistakes or out-of-distribution data that are identified can be flagged for manual review or can be otherwise remediated, thereby improving quality of care.

As mentioned previously, in some embodiments, it is contemplated that improvements in the quality and accuracy of anatomical landmark detection can provide significant benefits and/or performance increases for multiple different downstream operations that variously depend on the initial landmark detection (e.g., downstream operations can include, but are not limited to, pathology classification, screening, and/or detection). In some cases, an automated pathology detection system can perform such downstream operations using one or more machine learning networks. In some embodiments, deep reinforcement learning (DRL) can be used to train anatomical landmark detection agents to move within a 2D or 3D medical image in a series of steps that locate the center of one or more anatomical landmarks within the medical image.

For example, anatomical landmark agents can be trained to locate the center of anatomical landmarks by traversing an input medical image in a series of steps. A CNN or other neural network can receive a medical image (or a region of interest thereof) as input and generate one or more features or embeddings as output. Based at least in part on receiving the generated features or embeddings as input, a dist-DQN or dense network can then predict a discrete direction of motion for the anatomical landmark detection agent to take within the image. The predicted direction of motion can be determined as the direction that maximizes immediate and future rewards (e.g., the Q-value). The agent then moves in the predicted direction of motion in its next step, and the process repeats until the agent ultimately locates the center(s) of the one or more anatomical landmarks within the image.

The disclosure turns now to FIG. 1, which depicts an example architecture of a deep reinforcement learning (DRL) network 100 that can be used to detect or locate an anatomical landmark 125 within a medical image 110. As illustrated, the DRL network 100 can include one or more DRL agents 140, which in some embodiments can be anatomical landmark detection agents trained using a distributional deep-Q learning (dist-DQN) process. The DRL agents 140 (also referred to herein as "anatomical landmark detection agents 140" or "agents 140") can be associated with a DRL environment 110 that includes one or more portions of medical image data. For example, the DRL environment 110 can include MRI, CT, X-ray, or various other types of medical image data. The medical image data associated with DRL environment 110 can be a full (e.g., uncropped) medical image or a partial medical image. It is noted that although FIG. 1 depicts DRL environment 110 as including two-dimensional image data, three-dimensional image data can also be used without departing from the scope of the present disclosure.

The anatomical landmark detection agents 140 can be provided in the DRL environment 110 in order to detect or locate one or more anatomical landmarks 125 within an input of medical image data. In operation, each agent can move through the medical image data of environment 110 in a series of steps that can be treated as a stochastic process. In some embodiments, the series of steps taken by the anatomical landmark detection agent 140 within the medical image data can be treated as a Markov decision process (MDP). At each step, the agent 140 makes an observation of the surrounding environment 110 and, based at least in part on the DRL environmental observation, updates its state 120. For example, as illustrated in FIG. 1, the agent state 120 can be a cropped region of interest (ROI) around the agent's current location in environment 110.

In some embodiments, the medical image data of environment 110 can be represented as pixels (e.g., for 2D image data) or voxels (e.g., for 3D image data). Agent 140 can determine the DRL environmental observation as an image patch that represents a subset of the complete image and is centered on the agent. For example, when environment 110 contains 2D medical image data, at each step the anatomical landmark detection agent can observe an image patch of pixels that are adjacent to the agent's current pixel location; similarly, when environment 110 contains 3D medical image data, at each step the agent can observe an image patch of voxels that are adjacent to the agent's current voxel location. The size of the image patches determined by agent 140 can be constant or variable and may also be symmetric or asymmetric along the various dimensions of environment 110.

The agent state 120 (e.g., the portion of medical image data within the cropped ROI) can then be provided to a neural network encoder, shown here as a convolutional neural network (CNN) encoder 130. For example, the pixels or voxels associated with one or more of the observed image patch, the agent state 120, and/or the agent's current pixel/voxel location can be provided as input to the CNN 130 and used to generate a set of features or embeddings that correspond to the agent's current state.

As depicted in FIG. 1, CNN 130 can provide the generated features to DRL agent 140 as input. Using the generated features, DRL agent 140 subsequently predicts a discrete direction of motion for the to take within environment 110 (e.g., within the medical image data) in the next step. For purposes of clarity of explanation, DRL network 100 is depicted as including a single CNN encoder 130 and a single DRL agent 140, although it is noted that a greater number of CNNs and/or DRL agents can also be utilized without departing from the scope of the present disclosure. Similarly, one or more additional neural network or other machine learning models and/or architectures can also be utilized to generate the features or embeddings for the portion of medical image data associated with the current state 120 of anatomical landmark detection agent 140.

The discrete direction of motion predicted by the agent 140 is illustrated in FIG. 1 as an action 150, which can be selected as a movement along a selected one of a predetermined set of permissible directions of motion. For example, when the environment 110 includes pixels or other 2D medical image data, action 150 can be selected from a set of four permissible directions of motion (e.g., up, down, left, and right). When the environment 110 includes voxels or other 3D medical image data, action 150 can be selected from a set of six permissible directions of motion (e.g., up, down, left, right, forward, and backward).

As will be explained in greater depth below with respect to FIGS. 2 and 3, agent 140 can analyze each permissible direction of motion and determine or otherwise predict the direction of motion that maximizes immediate and discounted future rewards to the agent. In one illustrative example, agent 140 can use one or more Q-values (e.g., associated with the permissible directions of motion within the agent's current environment) to determine the direction of motion for action 150.

Uncertainty-Aware Distributional Deep Reinforcement Learning (DRL)

Systems, apparatuses, processes (also referred to as methods), and computer-readable media (collectively referred to as "systems and techniques") are described herein for uncertainty-aware deep reinforcement learning (DRL) for anatomical landmark detection in medical images. In the context of the following description, reference is made to examples in which one or more deep reinforcement learning (DRL) networks are used to implement anatomical landmark detection agents that can perform accurate anatomical landmark detection in several imaging modalities, including (but not limited to) computed tomography (CT) and magnetic resonance imaging (MRI). The one or more DRL networks can include, but are not limited to, deep Q-learning networks (DQNs) and/or distributional (e.g., distribution-based) deep Q-learning (dist-DQN), etc.), although it is noted that other machine learning architectures and/or models may also be utilized without departing from the scope of the present disclosure—the systems and techniques described herein can perform improved uncertainty determination based at least in part on features and/or other anatomical landmark detection information generated by one or more additional ML and/or DRL architectures. For instance, additional architectures that can be utilized include, but are not limited to, ResNet (and ResNet-like) architectures, DenseNet (and DenseNet-like) architectures, and other such architectures suited for performing the underlying classification tasks in a medical or pathology detection and analysis context, as would be appreciated by one of ordinary skill in the art.

As mentioned previously, practical application of landmark detection in a pathology classification, screening, or detection pipeline can require out-of-distribution images and/or incorrect landmark location predictions to be reliably detected for manual review and remediation or exclusion from consideration (e.g., so as to minimize the introduction and propagation of error into the pipeline). Accordingly, the systems and techniques described herein can be used to accurately detect anatomical landmarks and/or anatomical structures in medical images, while also providing an improved uncertainty determination that can be used to identify out-of-distribution images, incorrect landmark location predictions, and/or predicted landmark failures. For example, one or more Q-value probability distributions associated with a dist-DQN anatomical landmark detection agent can be used to determine a thresholded metric for detecting out-of-distribution images and/or predicted landmark failures associated with the dist-DQN agent, without suffering a loss of mean landmark location accuracy. In some embodiments, the thresholded metric can be shown to have an area under the receiver operator curve of 0.96 in the task of detecting out-of-distribution images and predicted landmark failures. Moreover, the trained, uncertainty-aware dist-DQN disclosed herein can be seen to achieve an improved accuracy in detecting the locations of anatomical landmarks in medical images over that of a non-dist-DQN model.

In one illustrative example, a DRL network (e.g., dist-DQN) can be trained on medical images associated with one or more anatomical structures or landmarks. For example, in some embodiments, one or more dist-DQN agents can be trained targeting the locations of knee fibular styloid and the intercondylar eminence of the tibia, although it is appreciated that various other anatomical structures, features, landmarks, etc., can also be utilized without departing from the scope of the present disclosure. In some embodiments, an improved uncertainty measure can be determined for the locations of anatomical landmarks (e.g., that have been detected in medical images by a trained dist-DQN agent) based at least in part on a full-width-half-maxima (FWHM) of the Q-value probability distributions associated with the trained dist-DQN.

Figure 2:
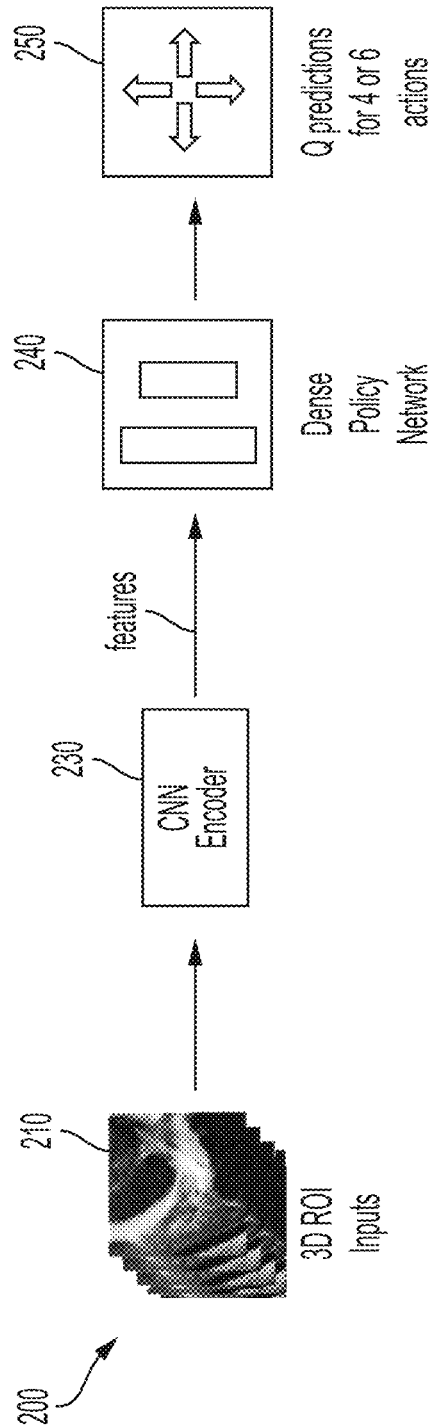
FIG. 2 illustrates an example architecture of a distributional deep Q-learning (dist-DQN) anatomical landmark detection agent, according to aspects of the present disclosure.
Figure 3:
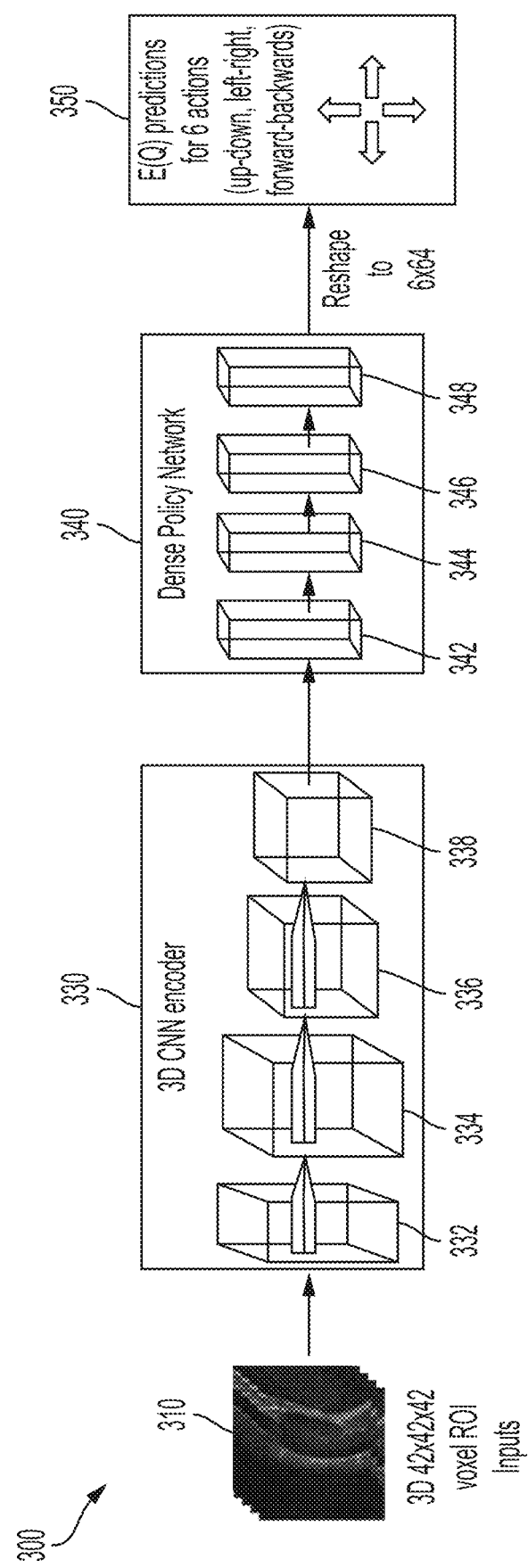
FIG. 3 illustrates another example architecture of a distributional deep Q-learning (dist-DQN) anatomical landmark detection agent, according to aspects of the present disclosure.

The disclosure turns next to FIG. 2, which depicts an example architecture 200 of a dist-DQN anatomical landmark detection agent according to aspects of the present disclosure (FIG. 3 depicts another example architecture of a dist-DQN anatomical landmark detection agent). As illustrated in FIG. 2, the input to the dist-DQN agent (also referred to as "the agent" or "the anatomical landmark detection agent") can include a plurality of region of interest (ROI) inputs 210, shown here as three-dimensional ROI inputs. The ROI inputs 210 can be obtained as a subset of the full medical image for which the dist-DQN agent is utilized to perform anatomical landmark detection. For example, three-dimensional ROI inputs can include a plurality of voxels that are a subset of a larger plurality of voxels that form a full 3D medical image, while two-dimensional ROI inputs can include a plurality of pixels that are a subset of a larger plurality of pixels that form a full 2D medical image.

The ROI inputs 210 can be centered on the agent's current location within the full medical image. For example, the ROI inputs 210 can be centered on a particular voxel, pixel, coordinate, etc., that is currently occupied or visited by the agent. As illustrated, the ROI inputs 210 can be encoded using a convolutional neural network 230 (e.g., CNN), although it is again noted that other neural network and/or other machine learning architectures and models can also be utilized to encode the ROI inputs 210. In some examples, the CNN 230 can be a 3D CNN, e.g., corresponding to 3D ROI inputs 210 containing voxels.

As illustrated, the CNN encoder 230 outputs one or more embeddings and/or features generated from the ROI inputs 210. The generated features are provided to a dense network, shown here as a dense policy network 240. The dense policy network 240 uses the image features from CNN 230 to generate Q-values corresponding to the allowable actions that may be taken by the dist-DQN agent. As mentioned previously, the allowable actions can comprise a pre-determined set of directions of motion, which can depend in part on the dimensionality of the ROI inputs 210 and the underlying medical image. In some embodiments, the agent's allowable actions at each step can be moving in one of the signed orthogonal image directions. For example, when the ROI inputs 210 include two-dimensional or pixel inputs, the allowable actions can comprise movement in one of four directions: up-down, left-right. For three-dimensional or voxel inputs, the allowable actions can comprise movement in one of six directions: up-down, left-right, front-back).

The dense policy network 240 can include a plurality of layers, as will be described below with respect to FIG. 3. In some embodiments, a final layer of dense policy network 240 can be provided as a softmax layer that encodes discrete Q-value probability distributions for each of the allowable actions that can be performed by the agent. In the example of the 3D ROI inputs 210 depicted in FIG. 2, there are six allowable actions for the agent and accordingly, the dense policy network 240 can include a final softmax layer that encodes six corresponding discrete Q-value probability distributions. In one illustrative example, the final softmax layer can be a 6×64 logit softmax layer that encodes 64 bin discrete Q-value probability distributions for each of the six allowable actions. Similarly, in the example of a 2D ROI input, there are four allowable actions for the agent, in which case the dense policy network 240 can include a final softmax layer that encodes four corresponding discrete Q-value probability distributions.

FIG. 3 illustrates another example architecture 300 of a dist-DQN anatomical landmark detection agent. In some embodiments, the example architecture 300 can be used to implement an anatomical landmark detection agent that is the same as or similar to one or more of the anatomical landmark detection agents described previously. Furthermore, in some embodiments, some or all of the description provided above with respect to the example architecture 200 of FIG. 2 can be applied wholly or in part to the example architecture 300 of FIG. 3.

As illustrated in FIG. 3, the dist-DQN anatomical landmark detection agent can receive ROI inputs 310, which can be provided as three-dimensional image volumes each containing a plurality of voxels. In some embodiments, the example dist-DQN agent architecture 300 can be used to implement anatomical landmark detection using a Markov decision process (MDP), wherein the agent moves through the image and is tasked with centering itself on the landmark of interest, as described previously with respect to FIGS. 1 and 2. The anatomical landmark detection agent's state can consist of the ROI inputs 310, or may otherwise be determined based at least in part on the ROI inputs 310. For example, in some embodiments the agent's state can consist of a 42×42×42 voxel isentropic image volume field of view (FOV) centered on the agent. In some cases, the isentropic image volume FOV can be grayscale. It is additionally noted that various other sizes of image volume FOVs may be utilized without departing from the scope of the present disclosure. The example dist-DQN agent architecture 300 depicts a scenario in which the ROI inputs 310 are three-dimensional; accordingly, the agent's allowable actions at each step in the MDP can be given by the six signed orthogonal image directions associated with the ROI inputs 310 (e.g., up, down, left, right, forward, backward).

The ROI inputs 310 (e.g., the isentropic image volume FOV containing voxels centered on the agent in the current step) can be provided to a learned model (e.g., a learned machine learning model) associated with the agent and used to predict or determine an action to be taken by the agent in the next step of the Markov decision process. In one illustrative example, the agent's learned model can be a machine learning network with one or more sub-networks. For instance, dist-DQN agent's learned model can include an encoder network 330 and an action-value network. As depicted in the example architecture 300 of FIG. 3, the encoder network 330 can be provided as a neural network, such as a convolutional neural network (CNN). In some embodiments, encoder network 330 can be a 3D CNN or other 3D convolutional encoder. It is noted that in the example architecture 300, the encoder network 330 is illustrated as a simplified 2D convolutional encoder for purposes of clarity and is not intended to be construed as limiting.

In some embodiments, the encoder network 330 (e.g., a 3D CNN) can include a plurality of convolutional layers and maxpooling blocks (e.g., here as combined blocks 332, 334, 336, 338), which receive the ROI inputs 310 and generate a corresponding set of image features or embeddings. In some examples, each convolutional layer can be followed by a maxpooling block, i.e., the combined CNN blocks 332-338 can each have a convolutional layer followed by a maxpooling layer. In some examples, the number of convolutional layers provided in encoder network 330 can be greater than the number of maxpooling layers provided in encoder network 330 (e.g., one or more of the combined CNN blocks 332-338 may be provided as a convolutional layer only, without a subsequent maxpooling layer). The encoder network 330 is followed by an action-value network, which comprises a dense policy network 340 and a final softmax step prediction layer 350. The dense policy network 340 comprises four dense layers 342, 344, 346, and 348, which can be connected successively. In some cases, dense policy network 340 can be provided with a greater or lesser number of dense layers, without departing from the scope of the present disclosure.

The softmax step prediction layer 350 can be provided as the final layer of both the action-value network and the dist-DQN agent architecture 300. The output of the last dense layer 348 can be coupled to the input of the softmax step prediction layer 350. In some embodiments, a reshaping or other transformation operation can be performed such that the output of the last dense layer 348 is appropriately sized for the softmax step prediction layer 350. For example, the output of dense layer 348 can be reshaped to dimensions of 6×64, matching the 6×64 dimensions of the softmax step prediction layer 350.

Softmax step prediction layer 350 can encode Q-value probability distributions for each of the six allowable actions (e.g., the movement directions available to the agent). In one illustrative example, softmax step prediction layer 350 can encode 64-bin discrete Q-value probability distributions that are evenly distributed over the range [−10, 20] for each of the six allowable actions for the agent. The agent can determine which of the six allowable actions to take in the next step of the MDP based on the Q-value probability distributions from the softmax step prediction layer 350. For example, the agent can determine a predicted Q-value of each action for a given state by calculating an expected value E(Q) of the Q-value probability distribution for the given action. Based on the predicted Q-values that the agent determines for each action, the agent can then determine one of the six allowable actions that should be taken in the next step. For example, the agent can select actions based on their maximum predicted Q-value (e.g., select one of the actions based on the maximum Q-value probability distribution expected value E(Q) determined for each action).

The dist-DQN agent associated with the example architecture 300 can be trained using annotated medical images that indicate one or more anatomical landmark locations. For example, one or more dist-DQN agents can be trained to perform anatomical landmark detection on medical images of the knee and detect anatomical landmarks such as fibular styloid and intercondylar eminence. In this example, the one or more dist-DQN agents can be trained using a training data set that comprises a plurality of medical images (e.g., MR, CT, etc.) that are annotated with the 3D point location of fibular styloid and intercondylar eminence (e.g., annotated with the location(s) of the target anatomical landmarks for detection). In some embodiments, the training data set images can be annotated to precisely indicate the target anatomical landmarks using a consistent reference point. In other words, the annotations can each indicate the same relative portion of the target anatomical landmark. For example, the annotations can indicate the 3D point location corresponding to the tip of the fibular styloid in a sagittal image at the slice level where the lateral meniscus becomes visible and the intercondylar eminence (tibial spike) at the level of the anterior cruciate ligament.

Described below are aspects of training procedures that, in some embodiments, can be utilized with one or more aspects of the present disclosures. A non-distributional DQN can be trained based on estimating the value of a given state-action pair as a function of immediate reward and maximum discounted future rewards, as follows:

$$Q^\pi(x,a) = ER(x,a) + \gamma E Q^\pi(x',a') \qquad \text{Eq. (1)}$$

where $Q^\pi(x, a)$ is the Q-value, e.g., the predicted value of taking action a in state x with model parameters π; ER(x, a) is the expected immediate reward given state-action pair (x, a); and $\gamma E Q^\pi(x', a')$ is the expected value of the optimal action a' from the successive state x', reached from the action-value pair (x, a) discounted by factor γ.

A distributional DQN (dist-DQN) can be implemented by modifying Eq. (1) as given below:

$$Z^\pi(x,a) = R(x,a) + \gamma Z^\pi(x',a') \qquad \text{Eq. (2)}$$

where $Z^\pi(x, a)$ is the predicted value distribution of taking action a in state x given model parameters π; R(x, a) is the distribution of immediate rewards given state-action pair (x, a); and $\gamma Z^{\pi}(x', a')$ is the value distribution of the successive state-action pair $(x', a')$ discounted by factor $\gamma$. In Eq. (2), the immediate expected reward R and the expected Q-values $Q^{\pi}$ of Eq. (1) are replaced with random variables (i.e., distributions). Accordingly, $Z^{\pi}(x', a')$ is a value distribution, rather than the expected value, of the value-action pair $(x, a)$.

In some embodiments, training and inference with the anatomical landmark detection agent(s) described herein can be performed such that the Q-value distribution for each allowable action—e.g., up-down, left-right, front-back movement—for the agent in a given state is learned as a discrete random variable. In some examples, strong performance can be obtained with the discrete distribution having N=64 bins in range [−10,20] encoded in the final softmax layer 350 of the agent's neural network architecture 300, as described above.

During training, immediate and future rewards can be defined such that they maximize the chance of the dist-DQN landmark detection agent finding the relevant anatomical landmark, e.g., the locations of knee fibular styloid and intercondylar eminence. In some embodiments, the anatomical landmark detection agent can be rewarded for moving closer to the landmark and/or can be additionally rewarded for finding the landmark during training. At the beginning of each training episode, one or more anatomical landmark detection agents are instantiated at a random location within a training image. As will be described in greater depth below, multi-scale training and inference can be performed wherein the agent starts operating within a low-resolution down-sampled image, with the resolution increasing as the agent approaches the target landmark.

In some examples, anatomical landmark detection agent(s) disclosed herein can be trained using a deep reinforcement learning (DRL) process, in which the agent is rewarded for correct or desired actions. In some embodiments, a reward of +2 can be provided to the anatomical landmark detection agent each time the agent centers itself at the image voxel corresponding to the anatomical landmark that is the subject of the training. For example, during training of an agent to detect fibular styloid locations, the agent can receive a reward of +2 each time the agent centers itself at the image voxel corresponding to the fibular styloid that is present in a given training image (e.g., recalling that for fibular styloid, this particular location can be the location of the tip of the fibular styloid in a sagittal image at the slice level where the lateral meniscus becomes visible). Reward sparsity can be reduced by providing the agent with a reward at each time step, e.g., a reward equal to the signed decrease in Euclidean distance (in units of voxels) resulting from the action taken by the agent in the time step.

As contemplated herein, multi-scale landmark detection can additionally, or alternatively, be implemented using the systems and techniques described herein. In multi-scale landmark detection, multiple anatomical landmarks can be detected in parallel for a single image by providing at least one anatomical landmark detection agent for each targeted anatomical landmark. In one illustrative example, two anatomical landmark detection agents can be trained simultaneously in a single image, with each agent detecting one of two target anatomical landmark types. For instance, a single annotated medical image of the knee can be used to simultaneously train a first agent to detect fibular styloid and to train a second agent to detect intercondylar eminence (e.g., two agents can be trained on a series of annotated medical images provided one at a time).

During multi-scale landmark detection training, each agent moves through the same medical image, but maintains its own unique location and FOV within the medical image. Accordingly, the two agents can be trained simultaneously, but in some embodiments, the agents do not communicate with one another. Instead, resolution changes can occur when both agents oscillate within a small region of the image for a pre-determined number of steps. A training episode can be terminated in response to the oscillation occurring within the highest resolution image. In some embodiments, the final predicted landmark location determined by the agent can be given as the state reached within the final oscillation period having the lowest maximum expected Q-value (based on the Q-value probability distributions). Such a determination of the final predicted landmark location can be based on the observation that any state reached from the correct state (e.g., reached from the actual landmark location) should result in a lower immediate reward to the agent, and thus a lower expected Q-value E(Q), than an adjacent state.

During inference, one or more anatomical landmark detection agents can be instantiated at the mean location within the image, e.g., calculated from a training set. Each anatomical landmark detection agent can determine its optimal action in a given state as the maximum expected value of the discrete Q-value distribution E(Q) over all allowed actions. Recalling that the anatomical landmark detection agent(s) described herein can be implemented with an improved uncertainty determination, it is contemplated that the uncertainty can be determined based at least in part on a normalized Q-value distributions. For example, the Q-value distributions can be normalized for the $0^{th}$ moment to equal 1. At each step in the MDP during inference, the full-width-half-maximum (FWHM) is calculated from the normalized Q-value distribution corresponding to the action with the highest expected value. These FWHM values can be averaged over all steps in the inference rollout for each anatomical landmark detection agent, and the maximum over all agents can be taken as the uncertainty metric.

In particular, the uncertainty determinations disclosed herein can be provided based on the observation that a wider probability distribution reflects greater uncertainty in Q-value estimation. For example, because wider distributions (and therefore higher FWHM values) can correspond to uncertainty in the expected Q-value for taking an action in a given state, the resulting mean FWHM can be thresholded, such that values higher than the threshold are flagged as being of high uncertainty. Q-value estimations determined to have a mean FWHM below the threshold can be determined as being of high confidence (e.g., relatively low uncertainty).

In some embodiments, multiple uncertainty determinations can be provided, and can be used to accurately quantify uncertainty during an anatomical landmark detection agent's episode. A first uncertainty, given as $U^H$ or $H(Z^{\pi}(x, a))$, can be determined based on a Shannon entropy of the Q-value distributions. A second uncertainty, given as $U^{FWHM}$ or $FWHM(Z^{\pi}(x, a))$, can be determined based on a full-width-half-maximum from the discrete Q-value distributions (e.g., as described above). In one illustrative example, the two uncertainty calculations can be averaged over all steps in the inference episode for each agent. Subsequently, the maximum averaged uncertainty value over the two agents can be taken as the final uncertainty determination for a given medical image that was provided as input. In some examples, the uncertainty-aware dist-DQN inference disclosed herein can be performed based on the following:

Require: number of agents $K \in \mathbb{R}^+$, distributional NN policy models $Z^{\pi_k}$
Initialize step counter n = 0
do until episode end
   for k = 1, ... , K do
      Take optimal action $a_k^* = \text{argmax}_a(E(Z^{\pi_k}(x_k, a)))$
      Calculate and save $FWHM_{k,n}(Z^{\pi_k}(x_k, a_k^*))$ and $H_{k,n}(Z^{\pi_k}(x_k, a_k^*))$
   end for
   n = n + 1
for k = 1, ... , K do Calculate mean $FWHM_k =$
$\frac{1}{n'}\sum_{n'} FWHM_{k,n'}$, and mean $H_k = \frac{1}{n'}\sum_{n'} H_{k,n'}$ return: final agent locations,
   $U^{FWHM} = \max_k(FWHM_k)$ over all agents,
   $U^H = \max_k(H_k)$ over all agents Presented below in Table 1 is an example set of training and anatomical landmark detection agent architecture parameters, according to one or more aspects of the present disclosure:

TABLE 1

Example training and agent architecture parameters

| Parameter | Value | Parameter | Value | Parameter | Value |
|---|---|---|---|---|---|
| multi-scale voxel spacing | (6.75 mm, 2.25 mm, 0.75 mm) | number of workers | 16 | optimizer | Adam |
| Agent FOV | 42 × 42 × 42 | number of worker gpus | 3 | learning rate | 0.0001 |
| maximum steps | 0.05 | number of worker gpus | 1 | batch size | 128 |
| interference epsilon | 400 | reward for find | 2 | gamma (discount factor) | 0.95 |
| oscillation voxel bounds | 3 × 3 × 3 | number of distribution bins | 64 | network update frequency | 50,000 |
| oscillation step length | 20 | distribution bin bounds | (−10, 20) | training exploration policy | per worker epsilon greedy |
| | | | | Replay buffer size | 200,000 |

In one illustrative example, the systems and techniques described herein can be trained to detect anatomical landmarks in medical images of the knee. For instance, anatomical landmark detection agents can be trained on a training data set that includes a plurality of sagittal proton density (SagPD) images, sagittal proton density with fat saturation (SagPDFS) images, and sagittal T2 with fat saturation (SagT2FS) images, with each training image annotated for target anatomical landmarks of the knee (e.g., fibular styloid, intercondylar eminence, etc.). In some examples, a unique agent can be trained for each target anatomical landmark (e.g., rather than utilizing a single agent tasked with finding both landmarks). The use of unique agents for each target anatomical landmark can decrease the total task complexity and/or reward structure complexity. Additionally, the use of unique agents can increase the robustness of the resulting landmark location predictions generated by each agent.

In one example training data set, 1152 total annotated images were provided, comprising 410 SagPD images, 504 SagPDFS images, and 238 SagT2FS images. Generalization can be improved by performing random augmentation on the 3D image volumes during training. For example, the random augmentation can include, but is not limited to, the superposition or introduction of random noise, rotation and/or translation in the sagittal image plane, and image stack reverse-ordering (e.g., creating an anatomically correct left knee image from a right knee image, and vice-versa). In some embodiments, clip limited adaptive histogram equalization followed by normalization for zero mean and standard deviation=1 can be performed for the training data set images.

The anatomical landmark detection agents were, in this example, trained for a maximum of $2 \times 10^7$ steps, with mean landmark error calculated every 100,000 steps using a 100-image validation set. The network with the lowest mean landmark location error on the validation set can be checkpointed and used for testing. In some embodiments, an additional agent can be trained without dist-DQN to provide a baseline for landmark detection accuracy comparison. In some cases, double DQN and/or Noisy Nets can be utilized in the training of one or more of the distributional models (e.g., dist-DQN agents).

Figure 4A:
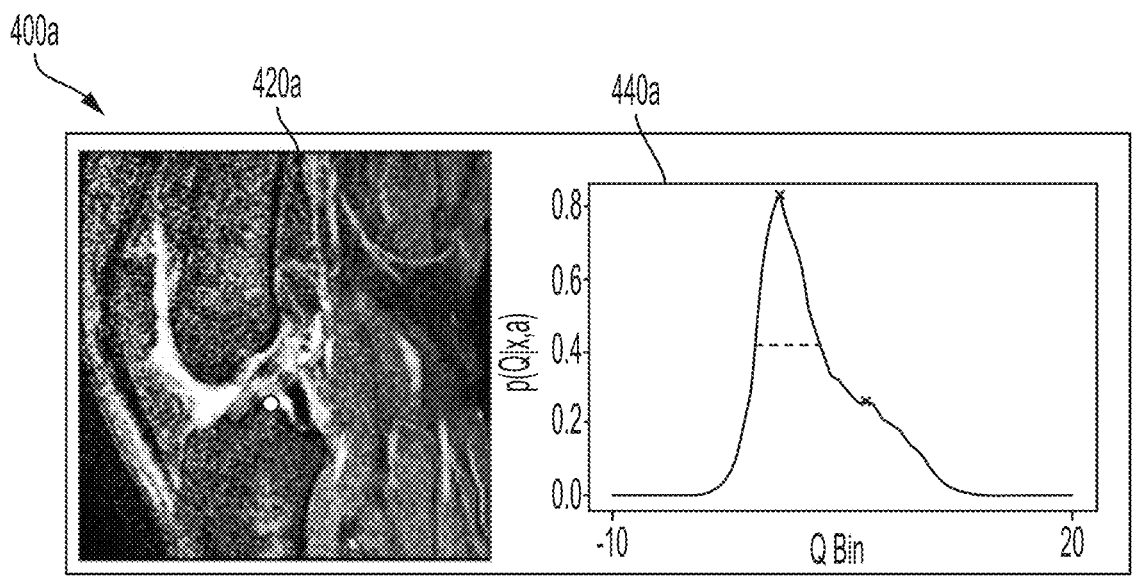
FIG. 4A illustrates a first input medical image and a corresponding Q-value distribution for the first input medical image, according to aspects of the present disclosure.
Figure 4B:
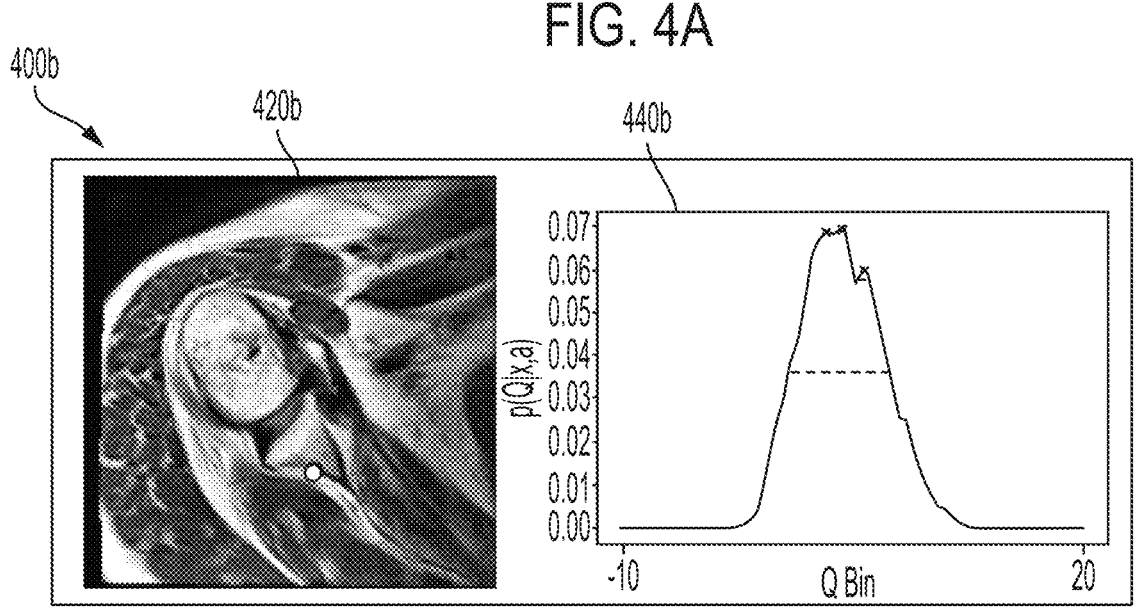
FIG. 4B illustrates a second input medical image and a corresponding Q-value distribution for the second input medical image, according to aspects of the present disclosure.

FIGS. 4A and 4B illustrate example experimental results of testing the uncertainty determination of the dist-DQN anatomical landmark detection agent described herein (e.g., $U^{FWHM}$ and $U^H$). In particular, FIGS. 4A and 4B illustrate example experimental results obtained for a tibial intercondylar eminence landmark detection agent. FIG. 4A depicts an input medical image 420a that passed a manual quality control (QC) process; FIG. 4B depicts an input medical image 420b that failed manual QC. Additionally, FIG. 4A includes a randomly selected example Q-value distribution 440a marked with FWHM and the final tibial intercondylar eminence landmark location, obtained by providing the input image 420a (which passed manual QC) to the tibial intercondylar eminence landmark detection agent. Similarly, FIG. 4B includes a randomly selected example Q-value distribution 440b marked that is also marked with FWHM and the final tibial intercondylar eminence landmark location, obtained by providing the input image 420b (which failed manual QC) to the same tibial intercondylar eminence landmark detection agent.

Peaks of the value distributions 440a and 440b are marked with an 'x' and the FWHM of each value distribution is indicated by the dashed horizontal line. White dots are superimposed on the medical images 420a and 420b indicating the final landmark locations determined by the tibial intercondylar eminence landmark detection agent. It is noted that the failed image 420b is an axial proton density MRI image of the shoulder, and is included to demonstrate the ability of the presently disclosed dist-DQN agent to detect out-of-distribution images by using the $U^{FWHM}$ determination to detect out-of-distribution images (e.g., because an axial shoulder image is out-of-distribution for a tibial intercondylar eminence landmark detection agent trained on medical images of the knee).

In the context of the example experimental results of FIGS. 4A and 4B, it can be seen that the Q-value distributions from pass cases (e.g., Q-value distribution 440a) exhibits a narrower distribution than the Q-value distributions from fail cases (e.g., Q-value distribution 440b), which can correspond to a lower uncertainty.

The uncertainty determinations $U^{FWHM}$ and $U^H$ were evaluated for their performance as binary classifiers for detecting out-of-distribution images and/or inaccurate landmark predictions in input medical images. Performance can be evaluated by manual review of the landmark prediction results generated by the anatomical landmark detection agent(s) described herein, with the reviewers blind to $U^{FWHM}$ and $U^H$ values. The review categorized each landmark prediction result into one of two classes: successes can be given as instances of clearly visible landmarks with landmark prediction error of less than 10 mm; failures can be given as landmark predictions with error greater than 10 mm or out-of-distribution characteristics (e.g., such as in FIG. 4B).

In some examples, a resulting area under the curve (AUC) for the $U^{FWHM}$ error flagging determination can be greater than that of the $U^H$ entropy metric (e.g., in this example, 0.91 and 0.76, respectively). The $U^{FWHM}$ uncertainty determination can be seen, in some examples, to have a higher specificity in high-sensitivity operating regimes. In one example, at 90% sensitivity to out-of-distribution images or landmark detection errors, the $U^{FWHM}$ uncertainty determination can provide a 77% specificity.

In one illustrative example, the dist-DQN detection agent disclosed herein can be used to perform anatomical landmark detection subject to an uncertainty-aware detection or determination of failure cases and/or potential failure cases. In some embodiments, failure cases of the dist-DQN agent can be determined or otherwise identified using an automatic quality control flagging process that is based on one or more thresholds for the uncertainty determinations described above. For example, automatic quality control flagging can be performed by thresholding the resulting $U^{FWHM}$ value associated with a predicted anatomical landmark location generated by the dist-DQN agent. In one illustrative example, a $U^{FWHM}$ threshold of 9.6 can be utilized, corresponding to the 90% sensitivity operating point. In one example of the automatic quality control flagging process, inference can be performed by the dist-DQN agent until the $U^{FWHM}$ uncertainty is determined to be below a threshold (e.g., below the 9.6 threshold). A $U^{FWHM}$ determination below the threshold can be used to identify an anatomical landmark location result as having low uncertainty. In some cases, if no images in a study performed by the dist-DQN agent is determined to have a $U^{FWHM}$ uncertainty below the threshold, the results of the study can be flagged as having low confidence.

Based on saving the result with the lowest $U^{FWHM}$ from each flagged study, the performance of the dist-DQN agent with uncertainty-aware detection and automatic determination of failure cases can be evaluated. In some examples, the dist-DQN agent described herein may achieve a $U^{FWHM}$ error detection sensitivity of 75% and a $U^{FWHM}$ specificity of 99.3%.

In some embodiments, the systems and techniques described herein can utilize one or more additional uncertainty determinations that can be determined from Q-value distributions. For example, the additional uncertainty determinations can be based on, but are not limited to, entropy variance, standard deviation, etc. In some examples, performance of may be improved by applying curve-fitting and/or smoothing the discrete Q-value distribution and then calculating one or more of the uncertainty determinations described herein on the smoothed distribution. In some embodiments, it is contemplated that uncertainty determinations can be performed at least in part determining FWHM over a fraction of the agent rollout during inference.

In some embodiments, the Q-value distribution can be further fit with a function whose width can be determined by a function parameter. For instance, width can be determined in a Gaussian function by the parameter σ:

$$f(x) = \frac{1}{\sigma\sqrt{2\pi}} \exp\left(\frac{-(x-u)^2}{2\sigma^2}\right) \qquad \text{Eq. (3)}$$

where the width of the Gaussian curve is determined by the parameter a.

In some embodiments, as the Q-value distribution can be asymmetric, the Q-value distribution can additionally or alternatively be fitted with a chi-square function:

$$f(x; z) = \begin{cases} \dfrac{x^{z/2-1} e^{-x/2}}{x^{z/2} \Gamma(z/2)}, & x > 0 \\ 0, & \text{otherwise} \end{cases} \qquad \text{Eq. (4)}$$

where Γ is the gamma function, and the parameter z determines the curve width.

In the above Gaussian and chi-square examples above, both a and z can be used as an uncertainty estimate, similar to FWHM. In some embodiments, estimation of both a and z can be performed by using an Expectation Maximization algorithm to estimate a mixture of Gaussians in a signal. In the case of the presently discussed example, the targeted number of Gaussians can be equal to one. In some embodiments, a variational Bayesian mixture of Gaussians can be used to improve an optimization of the number of mixtures from the Q-value distribution. In some examples, the presence of more than one mixture can be used as a proxy to flag out-of-distribution cases.

In addition to the presently disclosed metrics, which are based on Q-value distributions and then thresholded for out-of-distribution detection, it is further contemplated that one or more embodiments can train a predictive model of uncertainty by using the Q-value distribution as an input to the model. For example, from a training set of in-distribution and out-of-distribution images with binary labels, a dense neural network or other machine learning model can be trained for the task of detecting out-of-distribution images.

The presently disclosed discrete Q-value probability distributions can offer improvements over conventional approaches to estimating confidence and/or uncertainty in anatomical landmark detection results. In some embodiments, determining FWHM on the Q-value probability distributions can allows for tunable binary error flagging of landmark predictions with an AUC of 0.96 on a 291-image test set (41 errors, 250 non-errors). Because the binary error flagging classifier may be threshold based, the error flagging classifier can be tuned for various operating points to produce a desired weighting of sensitivity and specificity. Advantageously, the presently disclosed systems and techniques can be integrated into and thereby improve existing DRL training and inference frameworks, and moreover have not been seen to reduce landmark prediction accuracy or significantly increased training or inference speeds when compared to a non-distributional baseline.

What is claimed is:

1. A method for anatomical landmark detection, the method comprising:
generating, using a first machine learning sub-network of an anatomical landmark detection agent, one or more image features for a cropped region of interest of a three-dimensional (3D) medical image, wherein the cropped ROI comprises a subset of the 3D medical image centered on a current location of the anatomical landmark detection agent within the 3D medical image;
providing to a second machine learning sub network the one or more image features for use in generating Q-values corresponding to allowable movement directions to be taken by the anatomical landmark detection agent;
generating, using at least a softmax layer of the second machine learning sub-network of the anatomical landmark detection agent for a set of six allowable movement directions associated with movement of the anatomical landmark detection agent within the 3D medical image, six corresponding discrete Q-value distributions wherein the set of six allowable movement directions comprise orthogonal image directions of the 3D medical image and wherein each discrete Q-value distribution:
comprises a predicted value distribution associated with moving the anatomical landmark detection agent from the current location within the 3D medical image, in the respective allowable movement direction;
predicting an anatomical landmark location within the 3D medical image using the plurality of discrete Q-value distributions based on moving the anatomical landmark detection agent within the 3D medical image, wherein in a given state the anatomical landmark detection agent moves in a selected allowable movement direction having a Q-value which is a maximum discrete Q-value distributions expected value over the set of six allowable movement directions; and
determining an uncertainty measure for the predicted anatomical landmark location, wherein the uncertainty measure is determined based on an average full width half maximum (FWHM) value calculated using the respective discrete Q-value distribution having the maximum expected value over the set of six allowable movement directions for the given state.

2. The method of claim 1, wherein determining the uncertainty measure for the predicted anatomical landmark location comprises determining an average FWHM value over a plurality of inference steps performed by the anatomical landmark detection agent in an inference episode.

3. The method of claim 2, further comprising:
determining, for each of the plurality of inference steps, a selected allowable movement direction from the set of six allowable movement directions, the selected allowable movement direction having a highest expected Q-value distribution expected value.

4. The method of claim 3, further comprising:
determining, for each of the plurality of inference steps, the FWHM value for the Q-value distribution associated with the selected allowable movement direction; and
determining the uncertainty for the predicted anatomical landmark location based on an average FWHM of the Q-value distributions associated with the selected actions.

5. The method of claim 1, further comprising:
identifying an out-of-distribution image prediction or identifying the predicted anatomical landmark location as a prediction error, the identifying based on the uncertainty measure determined for the predicted anatomical landmark location; and
automatically triggering an error review for the 3D medical image and the predicted anatomical landmark location.

6. The method of claim 1, wherein the anatomical landmark detection agent is a distributional deep-Q learning network (dist-DQN) agent.

7. The method of claim 1, wherein:
the first machine learning sub-network of the anatomical landmark detection agent is a convolutional neural network (CNN); and
the CNN generates the one or more image features for an input comprising a subset of the 3D medical image, the subset including a plurality of voxels of an image volume field of view (FOV) centered on the anatomical landmark detection agent.

8. The method of claim 1, wherein:
the second machine learning sub-network of the anatomical landmark detection agent is a dense policy network comprising a plurality of dense layers; and
the softmax layer is provided as a final layer of the dense policy network, wherein the softmax layer encodes a discrete Q-value distribution for each allowable movement direction of the set of six allowable movement directions.

9. The method of claim 1, wherein the 3D medical image includes a magnetic resonance (MR) image or a computed tomography (CT) image.

10. The method of claim 1, wherein:
the 3D medical image is a three-dimensional (3D) image; and
the set of six allowable movement directions comprises six orthogonal image directions of the 3D image.

11. An apparatus for anatomical landmark detection, the apparatus comprising:
at least one memory; and
at least one processor coupled to the at least one memory, the at least one processor configured to:
generate, using a first machine learning sub-network of an anatomical landmark detection agent, one or more image features for a cropped region of interest of a three-dimensional (3D) medical image, wherein the cropped ROI comprises a subset of the 3D medical image centered on a current location of the anatomical landmark detection agent within the 3D medical image;
provide to a second machine learning sub network the one or more image features for use in generating Q-values corresponding to allowable movement directions to be taken by the anatomical landmark detection agent;
generate, using at least a softmax layer of the second machine learning sub-network of the anatomical landmark detection agent for a set of six allowable movement directions associated with movement of the anatomical landmark detection agent within the 3D medical image, six corresponding discrete Q-value distributions wherein the set of six allowable movement directions comprise orthogonal image directions of the 3D medical image and wherein each discrete Q-value distribution;

comprises a predicted value distribution associated with moving the anatomical landmark detection agent from the current location within the 3D medical image, in the respective allowable movement direction;

predict an anatomical landmark location within the 3D medical image using the plurality of discrete Q-value distributions based on moving the anatomical landmark detection agent within the 3D medical image, wherein in a given state the anatomical landmark detection agent moves in a selected allowable movement direction having a Q-value which is a maximum discrete Q-value distributions expected value over the set of six allowable movement directions; and determine an uncertainty measure for the predicted anatomical landmark location, wherein the uncertainty measure is determined based on an average full width half maximum (FWHM) value calculated using the respective discrete Q-value distribution having the maximum expected value over the set of six allowable movement directions for the given state.

12. The apparatus of claim 11, wherein the at least one processor is configured to determine the uncertainty measure for the predicted anatomical landmark location based on an average FWHM value determined over a plurality of inference steps associated with an inference episode of the anatomical landmark detection agent.

13. The apparatus of claim 12, wherein the at least one processor is further configured to:

determine, for each of the plurality of inference steps, a selected allowable movement direction from the set of six allowable movement directions, the selected allowable movement direction having a highest expected Q-value distribution expected value.

14. The apparatus of claim 13, wherein the at least one processor is further configured to:

determine, for each of the plurality of inference steps, the FWHM value for the Q-value distribution associated with the selected allowable movement direction; and determine the uncertainty measure for the predicted anatomical landmark location based on an average FWHM value of the Q-value distributions associated with the selected movement directions.

15. The apparatus of claim 11, wherein the at least one processor is further configured to:

identify an out-of-distribution image prediction or identify the predicted anatomical landmark location as a prediction error, the identifying based on the uncertainty measure determined for the predicted anatomical landmark location; and automatically trigger an error review for the 3D medical image and the predicted anatomical landmark location.

16. The apparatus of claim 11, wherein the anatomical landmark detection agent is a distributional deep-Q learning network (dist-DQN) agent.

17. The apparatus of claim 11, wherein:

the first machine learning sub-network of the anatomical landmark detection agent is a convolutional neural network (CNN); and the CNN generates the one or more image features for an input comprising a subset of the 3D medical image, the subset including a plurality of voxels of an image volume field of view (FOV) centered on the anatomical landmark detection agent.

18. The apparatus of claim 11, wherein:

the second machine learning sub-network of the anatomical landmark detection agent is a dense policy network comprising a plurality of dense layers; and the softmax layer is provided as a final layer of the dense policy network, wherein the softmax layer encodes a discrete Q-value distribution for each allowable movement direction of the set of six allowable movement directions.

19. The apparatus of claim 11, wherein the 3D medical image includes a magnetic resonance (MR) image or a computed tomography (CT) image.

20. The apparatus of claim 11, wherein:

The 3D medical image is a three-dimensional (3D) image; and the set of six allowable movement directions comprises six orthogonal image directions of the 3D image.

* * * * *